United States Patent [19]

Weber et al.

[11] Patent Number: 5,124,485

[45] Date of Patent: Jun. 23, 1992

[54] CATALYSTS AND METHODS OF SEPARATION THEREOF

[75] Inventors: Jürgen Weber, Oberhausen; Volker Falk, Wuppertal; Gerhardt Horn, Oberhausen; Hanswilhelm Bach, Duisburg; Klaus Mathieu; Claus Kniep, both of Oberhausen, all of Fed. Rep. of Germany

[73] Assignee: Hoechst Aktiengesellschaft, Fed. Rep. of Germany

[21] Appl. No.: 560,021

[22] Filed: Jul. 26, 1990

Related U.S. Application Data

[63] Continuation of Ser. No. 291,749, Dec. 29, 1988, abandoned.

[30] Foreign Application Priority Data

Dec. 30, 1987 [DE] Fed. Rep. of Germany ....... 3744506

[51] Int. Cl.$^5$ .......................................... C07C 209/00
[52] U.S. Cl. .................................................... 564/490
[58] Field of Search ........................................ 564/490

[56] References Cited

U.S. PATENT DOCUMENTS

| 2,436,368 | 2/1948 | Weber et al. | 260/583 |
|---|---|---|---|
| 3,232,888 | 2/1966 | Adam | 564/490 |
| 3,427,356 | 2/1969 | Baer | 564/490 |
| 4,137,267 | 1/1979 | Reid et al. | 564/490 |
| 4,140,720 | 2/1979 | Drake | 260/583 |

FOREIGN PATENT DOCUMENTS

| 13275 | 7/1980 | European Pat. Off. . |
| 37716 | 10/1981 | European Pat. Off. . |
| 151986 | 8/1985 | European Pat. Off. . |
| 168096 | 1/1986 | European Pat. Off. . |
| 1543337 | 3/1966 | Fed. Rep. of Germany . |
| 1667106 | 1/1967 | Fed. Rep. of Germany . |
| 745684 | 2/1956 | United Kingdom . |

OTHER PUBLICATIONS

Berkman et al. "Catalusis", pp. 263–265 (1940).

*Primary Examiner*—Marianne Cintins
*Assistant Examiner*—Jessica H. Nguyen
*Attorney, Agent, or Firm*—Jordan B. Bierman

[57] ABSTRACT

A method of preparation of a cobalt catalyst particularly adapted for hydrogenation of nitriles, the catalyst which is the product of the method, and the method of use thereof.

28 Claims, No Drawings

CATALYSTS AND METHODS OF SEPARATION THEREOF

This application is a continuation of application Ser. No. 07/291,749, filed Dec. 29, 1988, now abandoned.

This application claims the benefit of the priority of German Application P 37 44 506.5, filed Dec. 30, 1987.

The present invention is directed to a catalyst particularly designed for the hydrogenation of dialkylaminoacetonitriles to form the corresponding dialkylaminoethylamines. The process for the preparation of the catalysts, as well as the method of using them, is also included in the invention.

The desired products, dialkylaminoethylamines, have been found useful in the preparation of various pharmaceuticals. In particular, such compounds are important starting materials for synthesizing such medicinals as procainamide, ambenonium chloride, metoclopramide, and chinchocain.

The dialkylaminoethylamines which are the objects of the present invention may be obtained by a number of different routes. Particularly, GB-PS 745 684 teaches the preparation of these amines by catalytic hydrogenation of the corresponding nitrile at super-atmospheric pressure and temperatures below 110° C. While this process produces the desired compound in yields of approximately 92%, it requires the use of both liquid ammonia and Raney cobalt. The production of the latter is complicated and, moreover, it must be used in suspension, and cannot be used as a fixed bed catalyst.

A further process for the production of the amines in question is the reaction of potassium phthalic acid imide with dialkylaminoethyl halides. This reaction can also be carried out with ammonia or hexamethylene tetramine instead of the acid imide. However, processes of this type require large amounts of chemicals and the reaction products thereof are environmental polutants. As a result, the use of such processes on a commercial scale is severley limited.

Yet another process involves the reaction of ethylene imine with dialkylamines. While this process is quite economic and cost effective, the ethylene imine required is extremely toxic. Hence, this process has not found substantial favor commercially.

The Mannich reaction among dialkylamines, formaldehyde, and alkali metal cyanide will produce dialkylaminoacetonitriles. The nitriles are then hydrogenated to obtain the desired amines. The second step can take place in the presence of sodium or lithium aluminum hydride. However, such processes do not have any real commercial acceptance. In general, the hydrogenation is carried out using hydrogen in the presence of suitable catalysts. Diethylaminoacetonitrile can be hydrogenated by the use of Raney nickel to form the corresponding diamine. However, the yield is only 37% (Winans and Adkins, Am. Soc. 55, 4167 (1933)). Not only is the yield too small to be commercially satisfactory, great difficulty has been experienced in reproducing this reaction to obtain the claimed results (cf. Houben-Weyl 11/1, page 563).

BRIEF DESCRIPTION OF THE PRESENT INVENTION

Therefore, it is among the objects of the present invention to develop a process for the hydrogenation of nitriles to form the corresponding amines which overcomes the foregoing disadvantages and, at the same time, produces the desired end product under reasonable conditions and in high yields.

The present invention is directed to a catalyst for use in the foregoing reaction, a method for the preparation thereof, and the hydrogenation reaction carried out therewith. The catalyst is prepared by precipitation of a cobalt compound which is the reaction product of a water soluble cobalt salt and a water soluble alkali metal carbonate. The reaction takes place at 20° to 95° C. and is preferably separated from the resultant mixture and washed. Thereafter, it is reduced with hydrogen at a temperature of 200° to 300° C. It is preferred that the cobalt salt and the alkali metal carbonate are combined with each other by mixing together aqueous solutions of each. In order to separate the cobalt compound, filtration is the preferred means.

It has been found that the cobalt compound is primarily cobalt carbonate, although it may include other materials such as basic cobalt carbonates. Moreover, the preferred reduction temperature is 220° to 280° C., and is most preferably carried out in a plurality of stages. In each of the stages, the reduction temperature is higher than the previous stage. In particular, the use of three such stages has been found advantageous. Desirable temperatures for the first stage are 220° to 250° C., 245° to 260° C. for the second stage, and 255° to 280° C. for the third stage. Still more preferable are temperatures of 230° to 240° C., 250° to 255° C., and 260° to 270° C., respectively.

Insofar as reaction times are concerned, the first stage is appropriately carried out for 1 to 4 hours, the second stage for 1 to 5 hours, and the third stage for 1 to 5 hours. When using the more preferred temperature ranges, all three of the reaction times are most advantageously 2 to 3 hours.

It has been found that the catalyst, after reduction, is pyrophoric and, therefore, will spontaneously ignite in air. In order to overcome this, the reduced catalyst is contacted with an inert gas, such as nitrogen, which contains a relatively small amount of oxygen; for example, 0.5% to 1.0% by volume. This treatment oxides the catalyst surface and stabilizes it up to approximately 80° C.

It is also preferred to include in the catalyst, an additive taken from the class consisting of $SiO_2$, $MnO_2$, $ZrO_2$, $Al_2O_3$, and $MgO$. These additives are present in an amount of 0.25% to 15% by weight based on the cobalt compound before reduction. Such materials can be in the form of an oxide, hydroxide, and/or oxide hydrate. In addition to a single additive, mixtures or combinations thereof may also be included. The preferred amount is 1% to 8%, more preferably 2% to 5%, by weight based on the unreduced cobalt compound. Sodium and/or potassium are the preferred alkali metals. The preferred cobalt salts are nitrates, chlorides, sulfates, acetates, and mixtures thereof.

In carrying out the reaction with alkali metal carbonates, it has been found desirable that the aqueous solutions thereof each contain 25 to 150 g/l of the respective salt and carbonate. It is also desirable to use an excess of carbonate in the reaction. It is preferred that there be 1.1 to 1.5 mols of carbonate per mol of cobalt salt. Preferably, there are 1.2 to 1.3 mols of carbonate per mol of salt. It is also advantageous to use the carbonate and salt in equimolar proportions.

In carrying out the reduction, a space velocity of 200 to 2000 liters of hydrogen per liter of cobalt compound per hour has been found satisfactory. Preferably, this figure should be 300 to 1000, most preferably 400 to 700 liters of hydrogen per liter of cobalt compound per hour.

The additives are usefully suspended in either or both of the aqueous solutions of carbonate and cobalt salt. It has been found particularly desirable to incorporate the additive in the aqueous cobalt salt solution prior to precipitation and to precipitate the cobalt compound and the additive together. As a further alternative, the additive may be precipitated onto the cobalt compound after the cobalt compound has been precipitated but before it has been reduced.

If the catalyst is desired in a particular form, the cobalt compound may be shaped after precipitation and before reduction.

The catalyst which is the product of the foregoing method of preparation is particularly suited for the hydrogenation of dialkylaminoacetonitrile to form the corresponding dialkylaminoethylamine. The alkyls may be branched or straight chain, and may be the same or different. The amine formation of the present invention is particularly suited for alkyls which have 1 to 9 carbon atoms, preferably 1 to 6 and, most preferably, 2 to 4 carbon atoms.

The reaction temperature is advantageously 40° to 120° C., preferably 45° to 100° C., and most preferably 50° to 80° C. The reaction pressure is desirably 4 to 15 MPa, preferably 6 to 12 MPa, most preferably 8 to 10 MPa. It has also been found useful to dissolve the starting nitrile in an inert solvent. Appropriate solvents are aliphatic, cycloaliphatic, or aromatic hydrocarbons or aliphatic alcohols. Preferred solvents are cyclohexane, toluene, butanol, and 2-ethylhexane. The most preferred solvent is cyclohexane. Mixtures of solvents are also operable. It has been found desirable to maintain the concentration of the nitrile in the solvent in the range of 5% to 50%, preferably 10% to 40%, and most preferably 15% to 30%.

It has also been found advantageous to have ammonia present. It is recommended that 1 to 20 mols of ammonia per mol of nitrile be used. Preferably, 1.5 to 15 mols, and most preferably, 2.0 to 10 mols of ammonia are preferred.

The space velocity is advantageously 0.05 to 1.0 volumes of hydrogen per volume of catalyst per hour. Preferably, the space velocity is 0.1 to 0.5.

It is a particular feature of the present invention that the use of cobalt catalysts produced in accordance with the new method is able to convert the dialkylaminoacetonitriles to dialkylaminoethylamines with high yields and excellent selectivity.

While the precise nature of the action of the additives is not entirely clear, tests indicate that they act to reduce, minimize, or eliminate the sintering effects which otherwise would occur at high temperatures. Furthermore, the mechanical stability of the shapes molded from the catalyst mass is also substantially improved.

In addition to producing the desired amines selectively and in high yields, the process of the present invention permits the use of the starting nitriles in their commercially available forms. Otherwise, it might be necessary to provide special pretreatment; for example, to eliminate impurities resulting from manufacture. While the starting nitriles can be used directly in the process, it has been found desirable to introduce them into the reactor dissolved in an inert solvent.

When ammonia is added to the nitrile, it has been found that the selectivity towards the desired amines is in excess of 90%. In particular, the process of the present invention is directed to dialkylaminoacetonitriles of the formula

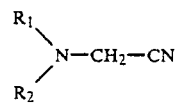

being readily hydrogenated into the corresponding diamines. In the foregoing formula, $R_1$ and $R_2$ (which may be the same or different), are branched or straight chain alkyl groups having 1 to 9 carbon atoms each. The method is particularly suitable when $R_1$ and $R_2$ are the same and each represents branched or straight chain alkyls having 1 to 6 carbon atoms, especially such alkyl groups having 2 to 4 carbon atoms.

The reaction may be continuous or batch type, the continuous reaction being preferred. In that case, the catalyst is placed in a tube into which the mixture of starting materials is fed at or near the bottom. Suitable preheating of the feed materials is frequently advisable.

The following Examples illustrate, but do not limit, the invention.

EXAMPLE 1

Preparation of a Cobalt Catalyst Without Additives

A solution, heated to 95° C., of 1852 g of $Co(NO_3)_2 \cdot 6H_2O$ (approximately 375 g of Co) in 7.5 liters of deionized water is poured into a solution, heated to 90° C., of 800 g of $Na_2CO_3$ in 7.5 liters of deionized water over a period of 2 minutes with vigorous stirring. A suspension of cobalt carbonate in water with a pH value of 8.2 to 8.4 is formed. The precipitation product is filtered off and washed thoroughly with roughly 90 liters of condensate water (temperature: 70° C.), so that the conductivity of the rinsing water is less than 100 $\mu$S on completion of the washing process. The still moist catalyst preliminary product is again suspended in deionized water and then spray-dried. The mass contains about 53.5% by weight of cobalt.

In the reduction process, 200 liters of $H_2$ per hour are passed over 0.5 liters of the dried catalyst mass at 240° C. for 2 hours in a tubular reactor having a diameter of 55 mm. The temperature is then increased to 250° C., and the reduction is continued for a further 2 hours using 200 liters of $H_2$ per hour. The reduction is completed by treating the catalyst for another 2 hours with 200 liters of $H_2$ per hour at 260° C. For stabilization purposes, the resultant powder is treated at 50° to 70° C. with an $N_2$ stream containing 0.7% by volume of $O_2$ and is then pressed into tablets.

EXAMPLE 2

Preparation of a Cobalt Catalyst With Additive

A solution, heated to 95° C., of 1852 g of $Co(NO_3)_2 \cdot 6H_2O$ (approximately 375 g of Co) and 85.73 g of $Mn(NO_3)_2 \cdot 4H_2O$ in 7.5 liters of deionized water is steadily poured into a solution, heated to 90° C., of 840 g of $Na_2CO_3$ in 7.5 liters of deionized water over a period of 2 minutes with vigorous stirring. A suspension of cobalt and manganese carbonate in water with a pH value of 8.2 to 8.4 is formed. The precipitation product is filtered off and washed thoroughly with roughly 90 liters of hot condensate water at 70° C., so that the conductivity of the rinsing water is less than 100 $\mu$S on completion of the washing process.

The still moist catalyst preliminary product is again suspended in deionized water and then spray-dried. The mass contains about 52% by weight of Co and about 4.1% by weight of $MnO_2$. The catalyst is then reduced as described in Example 1.

EXAMPLE 3

Hydrogenation of Diethylaminoacetonitrile 1.8 liters of the cobalt catalyst of Example 1 is arranged in the form of tablets 6 mm in diameter as a fixed bed in a heatable 3 m double-jacket tube with an inside diameter of 28 mm. The temperature is raised to 70° C. and hydrogen is fed in at a pressure of 8 MPa at the bottom of the reaction tube together with 600 ml per hour of a 15% by weight solution of diethylaminoacetonitrile in cyclohexane. The feed is continuous by means of a piston pump. The product discharging at the reactor head does not contain any diethylaminoacetonitrile. In addition to 86.5% of solvent, 11% of diethylaminoethylamine are detected by gas chromatography.

EXAMPLE 4

Hydrogenation of Diethylaminoacetonitrile 1.8 liters of the catalyst of Example 2 at 60° C., $H_2$ at a pressure of 8 MPa, and diethylaminoacetonitrile as a 30% by weight solution in cyclohexane are charged into the reactor of Example 3. At the same time, 2.5 mols of $NH_3$ per mol of nitrile are fed into the reactor and the throughput increased to 900 ml per hour. The diethylaminoacetonitrile is completely reacted. Gas chromatography analysis shows the reaction product to contain 73.2% cyclohexane and 25.1% diethylaminoethylamine.

EXAMPLE 5

Hydrogenation of Diethylaminoacetonitrile

Undiluted diethylaminoacetonitrile is reacted in the reactor of Example 3 at 50° C. and a $H_2$ pressure of 8 MPa. 2.5 mols of $NH_3$ are fed into the reactor per mol of nitrile, and the throughput is set at 180 ml/h. This corresponds to a space velocity of 0.1 volumes per hour. The nitrile is completely reacted, and the gas chromatography analysis shows the reaction product to contain 89.7% of diethylaminoethylamine, the remainder being cleavage products. The reaction product is worked up in a column with 24 theoretical plates. Diethylaminoethylamine of more than 99% purity is recovered.

Although only a limited number of specific embodiments of the present invention have been expressly disclosed, it is, nonetheless, to be broadly construed and not to be limited except by the character of the claims appended hereto.

What we claim is:

1. A process for the preparation of dialkylaminoethylene comprising reacting at least one dialkylaminoacetonitrile with hydrogen in the presence of a catalyst, said catalyst being prepared by
   reacting a water soluble cobalt salt and a water soluble alkali carbonate at a reaction temperature of 20° C. to 95° C. to form a reaction mixture from which a cobalt compound reaction product precipitates, washing the precipitated cobalt compound, and reducing the washed cobalt compound with hydrogen in three discrete stages, a first stage of 1 to 4 hours having a first temperature of 220° C. to 250° C., a second stage of 1 to 5 hours having a second temperature of 245° C. to 260° C., and a third stage of 1 to 5 hours having a third temperature of 255° C. to 280° C., said first temperature being less than said second temperature, and said second temperature being less than said third temperature.

2. The method of claim 1 wherein the alkyls are branched or straight chain and are the same or different.

3. The method of claim 1 wherein each of the alkyls have 1 to 9 carbon atoms.

4. The method of claim 3 wherein each of the alkyls has 1 to 6 carbon atoms.

5. The method of claim 4 wherein each of the alkyls has 2 to 4 carbon atoms.

6. The method of claim 3 wherein the alkyls are the same.

7. The method of claim 1 wherein said reaction temperature is 40° to 120° C.

8. The method of claim 7 wherein said reaction temperature is 45° to 100° C.

9. The method of claim 8 wherein said reaction temperature is 50° to 80° C.

10. The method of claim 1 wherein the reaction is carried out under a pressure of 4 to 15 MPa.

11. The method of claim 10 wherein said pressure is 6 to 12 MPa.

12. The method of claim 11 wherein said pressure is 8 to 10 MPa.

13. The method of claim 1 wherein the nitrile is dissolved in an inert solvent.

14. The method of claim 13 wherein said solvent is at least one aliphatic, cycloaliphatic, or aromatic hydrocarbon or an aliphatic alcohol.

15. The method of claim 14 wherein said solvent is taken from the group consisting of cyclohexane, toluene, butanol, and 2-ethylhexane.

16. The method of claim 15 wherein said solvent is cyclohexane.

17. The method of claim 13 wherein there is a concentration of said nitrile in said solution of 5% to 50% by weight.

18. The method of claim 17 wherein said concentration is 10% to 40%.

19. The method of claim 18 wherein said concentration is 15% to 30%.

20. The method of claim 1 wherein ammonia is present.

21. The method of claim 20 wherein there are 1 to 20 mols of ammonia per mol of the nitrile.

22. The method of claim 21 wherein there are 1.5 to 15 mols of ammonia per mol of said nitrile.

23. The method of claim 22 wherein there are 2.0 to 10 mols of ammonia per mol of said nitrile.

24. The method of claim 1 wherein said hydrogen is passed over said catalyst at a space velocity of 0.05 to 1.0 volumes of said hydrogen per volume of said catalyst per hour.

25. The method of claim 24 wherein said space velocity is 0.1 to 0.5.

26. The method of claim 1 wherein, after said reducing, said catalyst is contacted by an inert gas containing a small amount of oxygen.

27. The method of claim 26 wherein said small amount is 0.5 percent to 1.0 percent by volume based on said inert gas.

28. The method of claim 1 wherein an additive amount of at least one additive taken from the group consisting of $SiO_2$, $MnO_2$, $ZrO_2$, $Al_2O_3$, and MgO, is present, said additive amount being 0.25 percent to 15 percent by weight based on said cobalt compound before said reduction.

* * * * *